United States Patent [19]

VandenBerg

[11] Patent Number: Plant 7,225

[45] Date of Patent: May 1, 1990

[54] CHRYSANTHEMUM PLANT NAMED SUNDORO

[75] Inventor: Cornelis P. VandenBerg, Salinas, Calif.

[73] Assignee: Yoder Brothers, Inc., Barberton, Ohio

[21] Appl. No.: 247,525

[22] Filed: Sep. 22, 1988

[51] Int. Cl.[5] ..... A01H 5/00

[52] U.S. Cl. ..... Plt./76

[58] Field of Search ..... Plt./76

*Primary Examiner*—James R. Feyrer

*Attorney, Agent, or Firm*—Foley & Lardner, Schwartz, Jeffery, Schwaab, Mack, Blumenthal & Evans

[57] ABSTRACT

A Chrysanthemum plant named Sundoro particularly characterized by its flat capitulum form; decorative capitulum type; red-purple ray floret color; diameter across face of capitulum of up to 7 cm at maturity; medium plant height with spreading and prolific branching pattern; average natural season flower date of August 30 in Salinas, Calif. and September 29 in Hightstown, N.J.; uniform seven week photoperiodic flowering response to short days in photoperiodic controlled flowering programs; and durable, uniform performance in outside fall flowerings and in spring small pot flowering programs.

3 Drawing Sheets

The present invention comprises a new and distinct cultivar of Chrysanthemum, botanically known as *Dendranthema grandiflora,* and referred to by the cultivar name Sundoro.

Sundoro, identified as 85-125001, was originated by the inventor, Cornelis P. VandenBerg, from a cross made in a controlled breeding program in Salinas, Calif., in 1985.

The female parent and the male parent of Sundoro were both unnamed seedlings, identified respectively as 82-N14003 and 83-631002.

Sundoro was discovered and selected as one flowering plant within the progeny of the stated cross by Cornelis P. VandenBerg in January 1986, in a controlled environment in Salinas, Calif.

The first act of asexual reproduction of Sundoro was accomplished when vegetative cuttings were taken from the initial selection in April 1986 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Sundoro are firmly fixed and are retained through successive generations of asexual reproduction.

Sundoro has not been observed under all possible environmental conditions. The phenotype may vary significantly with variations in environment such as temperature, light intensity and daylength.

The following observations, measurements and comparisons describe plants grown in a controlled open area in Salinas, Calif. and in Hightstown, N.J. Rooted cuttings were established in soil and maintained outdoors under the natural temperature and daylength prevailing during July and September. Single pinching was practiced with all branches and buds retained.

The following traits have been repeatedly observed and are determined to be basic characteristics of Sundoro, which, in combination, distinguish this chrysanthemum as a new and distinct cultivar:

1. Flat capitulum form.
2. Decorative capitulum type.
3. Red-purple ray floret color.

4. Diameter across face of capitulum up to 7 cm at maturity.
5. Medium plant height.
6. Spreading and profilic branching pattern.
7. Average natural season flower date of August 30 in Salinas, Calif., and September 29 in Hightstown, N.J.
8. Uniform seven week photoperiodic flowering response to short days in photoperiodic controlled flowering programs.
9. Durable, uniform performance in outside fall flowerings and in spring small pot flowering programs.

The accompanying photographic drawings show typical inflorescence and leaf characteristics of Sundoro, with the colors being as nearly true as possible with illustrations of this type. Sheet 1 is a color photograph of Sundoro grown as a pinched spray pot mum. Sheet 2 is a black and white photograph of three views of the inflorescence of Sundoro. Sheet 3 is a black and white photograph showing the upper and under sides of the leaves of Sundoro at three stages of development (mature, intermediate and immature).

Of the commercial cultivars known to the inventor, the most similar in comparison to Sundoro is Debonair, disclosed in U.S. Plant Pat. No. 5,324. Reference is made to attached Chart A, which compares certain characteristics of Sundoro to the same characteristics of Debonair.

Similar traits are capitulum form and type, controlled flowering response and average natural season flower date. The ray floret color of Sundoro is a vibrant red-purple, while the color of Debonair is described as purple. Sundoro has a more prolific branching pattern, a larger diameter of capitulum, and a taller plant height than Debonair.

In the following description color references are made to The Royal Horticultural Society Colour Chart. The color values were determined on plant material grown in a controlled greenhouse environment in Salinas, Calif. on May 20, 1988.

Classification:

*Botanical.—Dendranthema grandiflora, cv Sundoro.*

*Commercial.*—Decorative spray pot mum and garden mum.

I. INFLORESCENCE

A. Capitulum:
*Form.*—Flat.
*Type.*—Decorative.
*Diameter across face.*—Up to 7 cm at maturity.

B. Corolla of ray florets:
*Color (general tonality from a distance of three meters).*—Red-purple.
*Color (upper surface).*—Just opening 60A to 60B, maturing to 58A.
*Color (under surface).*—Closest to 75C, streaked with 58A.
*Shape.*—Longitudinal: Straight. Cross-section: Middle of ray floret: Flat. Tip of ray floret: Convex.

C. Corolla of disc florets:
*Color (mature).*—Closest to 1B.
*Color (immature).*—Closest to 144B. Very few disc florets. Disc florets are covered by inner rows of ray florets.

D. Reproductive organs:
*Androecium.*—Present on disc florets only; very scant pollen.
*Gynoecium.*—Present on both ray and disc florets.

II. PLANT

A. General appearance:
*Height.*—Medium.

*Branching pattern.*—Spreading and prolific.

B. Foliage:
*Color (upper surface).*—147A.
*Color (under surface).*—147B.
*Shape.*—Small, lobed.

CHART A

COMPARISON OF SUNDORO AND DEBONAIR

| Cultivar | Sundoro | Debonair |
|---|---|---|
| Ray Floret Color | Red-purple | Purple |
| Capitulum Form and Type | Flat Decorative | Flat Decorative |
| Branching Pattern | Spreading and Prolific | Spreading |
| Diameter Across Face of Capitulum | Up to 7 cm | Up to 55 mm |
| Plant Height | Medium | Short |
| Controlled Response | 7 Weeks | 7 Weeks |
| Average Natural Season Flowerdate: | | |
| In Salinas, CA | August 30 | August 30 |
| In Hightstown, NJ | September 29 | September 29 |

COMPARISONS MADE OF PLANTS GROWN UNDER NATURAL SEASON OUTDOOR CONDITIONS IN SALINAS, CALIFORNIA AND IN HIGHTSTOWN, NEW JERSEY

I claim:

1. A new and distinct Chrysanthemum plant named Sundoro, as described and illustrated.

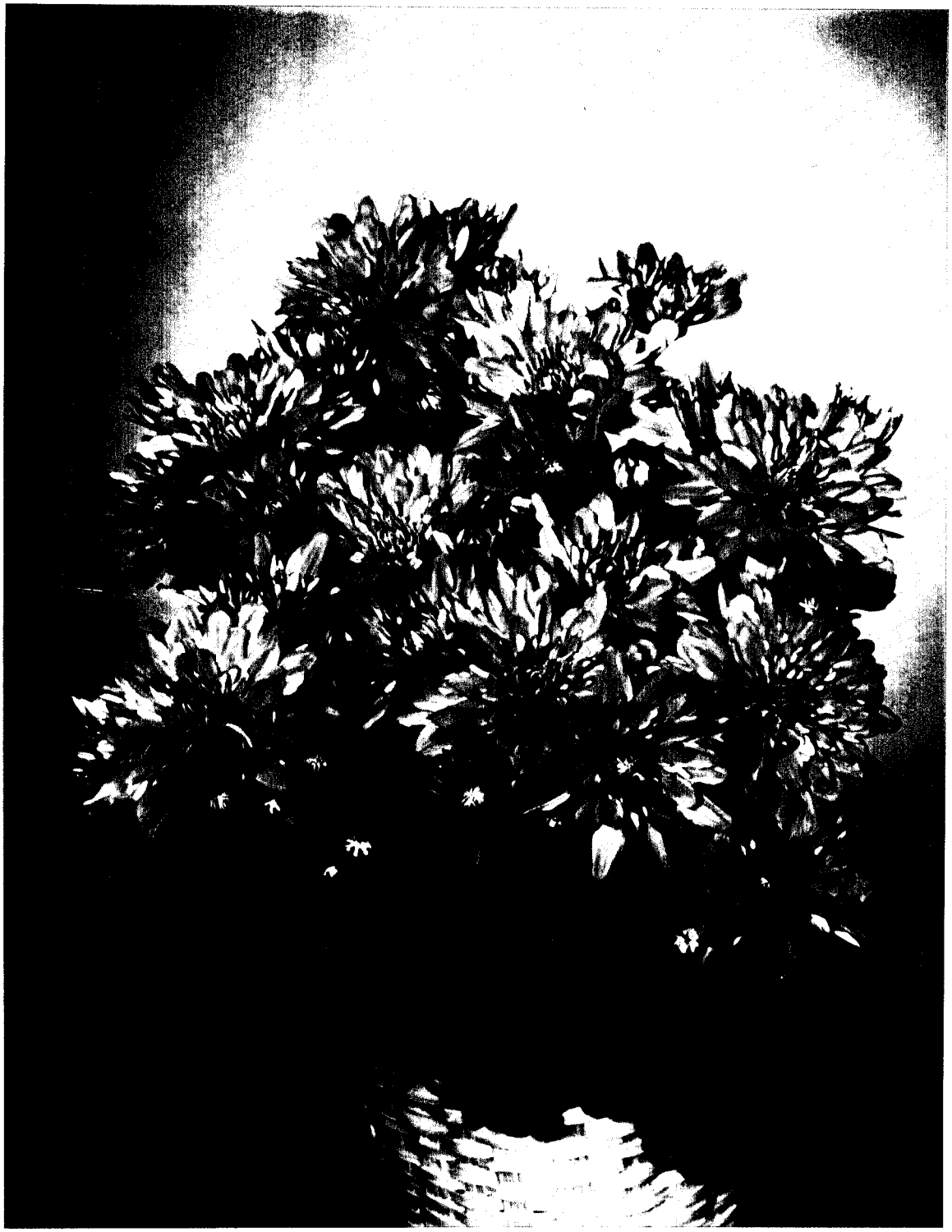

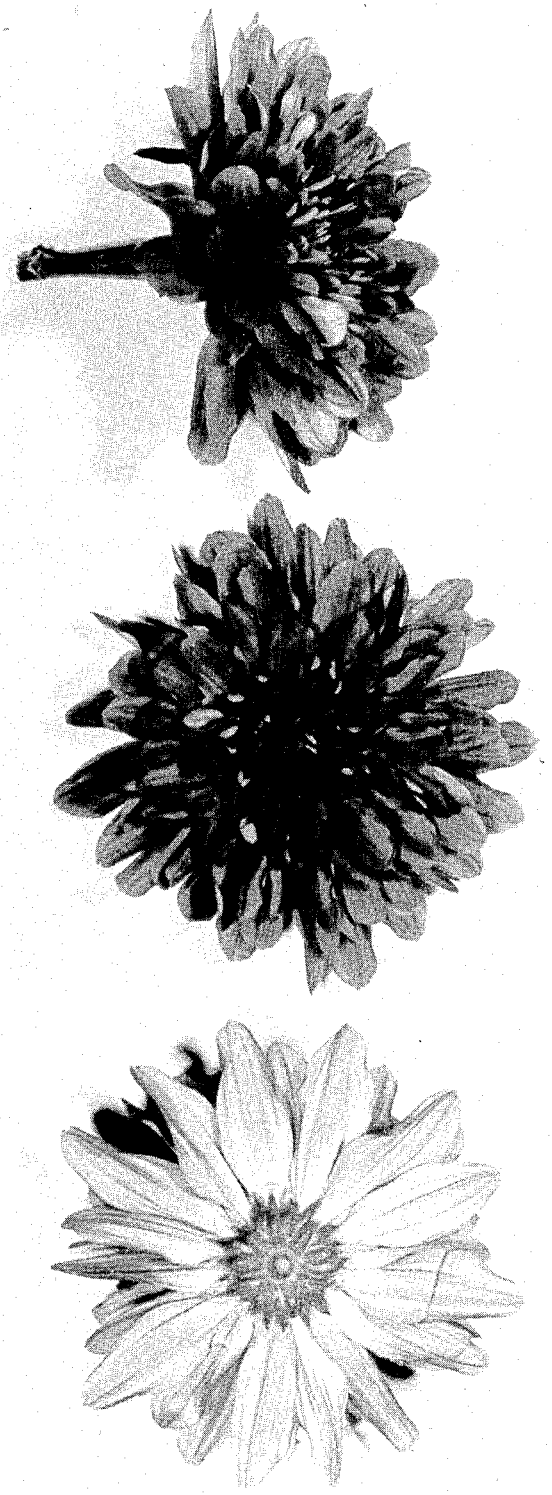

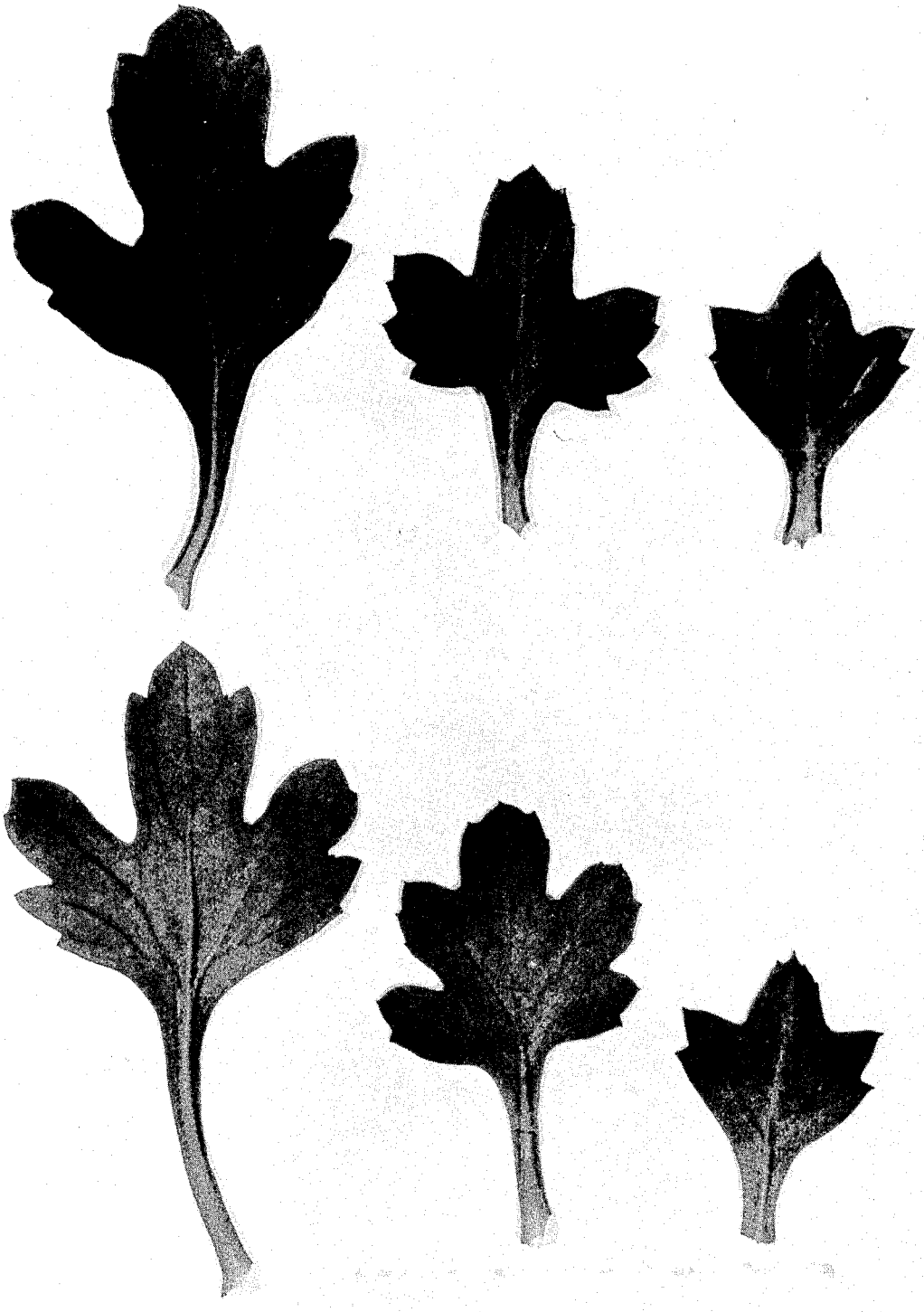

* * * * *